US00PP28531P2

(12) United States Plant Patent
Koekkoek

(10) Patent No.: US PP28,531 P2
(45) Date of Patent: Oct. 17, 2017

(54) CARNATION PLANT NAMED 'HILESMAY'

(50) Latin Name: ***Dianthus* L.**
Varietal Denomination: Hilesmay

(71) Applicant: Arthur N. J. Koekkoek, Alkmaar (NL)

(72) Inventor: Arthur N. J. Koekkoek, Alkmaar (NL)

(73) Assignee: Hilverda Kooij B.V., De Kwakel (NL)

( * ) Notice: Subject to any disclaimer, the term of this patent is extended or adjusted under 35 U.S.C. 154(b) by 0 days.

(21) Appl. No.: 14/999,647

(22) Filed: Jun. 8, 2016

(51) Int. Cl.
*A01H 5/02* (2006.01)

(52) U.S. Cl.
USPC ..... Plt./272

(58) Field of Classification Search
USPC ..... Plt./272
See application file for complete search history.

*Primary Examiner* — Annette Para
(74) *Attorney, Agent, or Firm* — C. A. Whealy

(57) ABSTRACT

A new and distinct cultivar of Carnation plant named 'Hilesmay', characterized by its compact, uniformly mounding and upright to broadly spreading plant habit; relatively small leaves; freely flowering habit; red purple and greyed purple bi-colored single flowers; and good container performance.

1 Drawing Sheet

Botanical designation: *Dianthus* L.
Cultivar denomination: 'HILESMAY'.

BACKGROUND OF THE INVENTION

The present invention relates to a new and distinct cultivar of Carnation plant, botanically known as *Dianthus* L., grown commercially as a container plant and hereinafter referred to by the name 'Hilesmay'.

The new Carnation plant is a product of a planned breeding program conducted by the Inventor in De Kwakel, The Netherlands. The objective of the breeding program is to create new container Carnation plants with numerous attractive flowers.

The new Carnation plant originated from a cross-pollination made by the Inventor in De Kwakel, The Netherlands in June, 2011 of *Dianthus* L. 'Marble Choclat', not patented, as the female, or seed, parent with a proprietary selection of *Dianthus* L. identified as code number A26340-01, not patented, as the male, or pollen, parent. The new Carnation plant was discovered and selected by the Inventor as a single flowering plant from within the progeny of the stated cross-pollination in a controlled greenhouse environment in De Kwakel, The Netherlands in September, 2012.

Asexual reproduction of the new Carnation plant by terminal cuttings propagated in a controlled greenhouse environment in De Kwakel, The Netherlands since October, 2012 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilesmay'. These characteristics in combination distinguish 'Hilesmay' as a new and distinct Carnation plant:

1. Compact, uniformly mounding and upright to broadly spreading plant habit.
2. Relatively small leaves.
3. Freely flowering habit.
4. Red purple and greyed purple bi-colored single flowers.
5. Good container performance.

Plants of the new Carnation differ primarily from plants of the female parent, 'Marble Choclat', in the following characteristics:

1. Plants of the new Carnation are not as compact as plants of 'Marble Choclat'.
2. Flowers of plants of the new Carnation have fewer petals than flowers of plants of 'Marble Choclat'.
3. Plants of the new Carnation and 'Marble Choclat' differ in flower color as flowers of plants of 'Marble Choclat' have white-colored margins.

Plants of the new Carnation differ primarily from plants of the male parent selection in the following characteristics:

1. Plants of the new Carnation are more upright than and not as trailing as plants of the male parent selection.
2. Flowers of plants of the new Carnation have fewer petals than flowers of plants of the male parent selection.
3. Plants of the new Carnation and the male parent selection differ in flower color as plants of the male parent selection have darker-colored flowers.

Plants of the new Carnation also can be compared to plants of *Dianthus caryophyllus* 'Margarita', disclosed in U.S. Plant Pat. No. 17,335. In side-by-side comparisons, plants of the new Carnation differ primarily from plants of 'Margarita' in the following characteristics:

1. Plants of the new Carnation are more freely branching than plants of 'Margarita'.
2. Plants of the new Carnation have shorter branches than plants of 'Margarita'.

3. Plants of the new Carnation are more freely flowering than plants of 'Margarita'.
4. Plants of the new Carnation and 'Margarita' differ in flower color as plants of 'Margarita' have white and red purple-colored flowers.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant.

The photograph comprises a side perspective view of a typical flowering plant of 'Hilesmay' grown in a container.

DETAILED BOTANICAL DESCRIPTION

Plants used in the aforementioned photograph and following observations and measurements were grown during the spring in 10.5-cm containers in a glass-covered greenhouse in De Kwakel, The Netherlands and under cultural practices typical of commercial container Carnation production. During the production of the plants, day temperatures ranged from 12° C. to 16° C., night temperatures averaged 12° C. and light levels averaged 7,000 lux. Plants used for the photograph and description were three months old. In the following description, color references are made to The Royal Horticultural Society Colour Chart, 2015 Edition, except where general terms of ordinary dictionary significance are used.

Botanical classification: *Dianthus* L. 'Hilesmay'.

Parentage:

*Female, or seed, parent.*—*Dianthus* L. 'Marble Choclat', not patented.

*Male, or pollen, parent.*—Proprietary selection of *Dianthus* L. identified as code number A26340-01, not patented.

Propagation:

*Type.*—By terminal cuttings.

*Time to initiate roots, summer.*—About six days at temperatures ranging from 20° C. to 25° C.

*Time to initiate roots, winter.*—About eight days at temperatures about 18° C.

*Time to produce a rooted young plant, summer.*—About three weeks at temperatures ranging from 20° C. to 25° C.

*Time to produce a rooted young plant, winter.*—About five weeks at temperatures about 18° C.

*Root description.*—Medium in thickness, fibrous; whitish in color.

*Rooting habit.*—Moderate branching; medium density.

Plant description:

*Plant and growth habit.*—Herbaceous perennial, typically grown as a container plant; compact, uniformly mounding, upright to broadly spreading plant habit; growth habit, moderate to low vigor.

*Plant height, soil level to top of foliar plane.*—About 14.6 cm.

*Plant height, soil level to top of floral plane.*—About 18.1 cm.

*Plant diameter or spread.*—About 21 cm.

*Lateral branches.*—Branching habit: Freely branching habit with about seven main (basal) stems; each main stem with about five lateral branches; pinching enhances lateral branch development. Length: About 8.6 cm. Diameter: About 1.5 mm. Internode length: About 3 mm. Strength: Strong. Aspect: Upright to about 60° from vertical. Texture and luster: Smooth, glabrous; moderately glossy. Color, developing: Close to 142B; at internodes, close to 145B. Color, developed: Close to N138B.

Leaf description:

*Arrangement.*—Opposite, simple; sessile.

*Length.*—About 7.6 cm.

*Width.*—About 4 mm.

*Shape.*—Narrowly oblanceolate; moderately carinate.

*Apex.*—Acute.

*Base.*—Attenuate; decurrent.

*Margin.*—Entire.

*Texture and luster, upper and lower surfaces.*—Smooth, glabrous; matte.

*Venation pattern.*—Parallel.

*Color.*—Developing leaves, upper and lower surfaces: Close to 143A; towards the base, close to 144B. Fully expanded leaves, upper surface: Close to between NN137A and 139A; venation, close to between NN137A and 139A. Fully expanded leaves, lower surface: Close to between NN137C and N138A; venation, close to 143A to 143B.

Flower description:

*Flower form and flowering habit.*—Single flowers arranged singly or in pairs; freely flowering habit with about 55 flowers developing during the flowering season; flowers face mostly upright to slightly outwardly.

*Natural flowering season.*—Flowering is continuous from the spring to late summer in The Netherlands; plants begin flowering about nine to eleven weeks after planting.

*Postproduction longevity.*—Flowers last about ten days on the plant; flowers not persistent.

*Fragrance.*—Moderately fragrant; clove-like, sweet.

*Flower buds.*—Length: About 2.4 cm. Diameter: About 7 mm. Shape: Oblong to narrowly obovate. Texture and luster: Smooth, glabrous; matte. Color: Close to NN137C; petal apices, close to 71A.

*Flower diameter.*—About 4 cm.

*Flower depth.*—About 3.2 cm.

*Petals.*—Quantity and arrangement: Five petals arranged in a single whorl. Length: About 3.9 cm. Width: About 2.1 cm. Shape: Spatulate. Apex: Praemorse; slightly crinkled. Base: Narrowly cuneate. Margin: Entire; slightly undulate. Texture and luster, upper and lower surfaces: Smooth, glabrous; slightly velvety; matte. Color: When opening, upper surface: Close to 187A; two large blotches, close to between 60A and 61B; towards the base, close to 70B; at the base, close to 145B. When opening, lower surface: Close to 59C; at the base, close to 145B. Fully opened, upper surface: Close to between 59A and 187B; two large blotches, close to 64B to 64C; towards the base, close to N74D; at the base, close to 145B; color does not change with development; venation, similar to lamina colors. Fully opened, lower surface: Close to 186D; towards the margins, fading to close to 75C; at the base, close to 145B; color does not change with development; venation, similar to lamina colors. Petaloids: Petaloid development has not been observed on plants of the new Carnation.

*Sepals*.—Quantity and arrangement: Five sepals arranged in a single whorl; proximal 70% portion of the sepals are fused into a campanulate-shaped calyx. Calyx length: About 2.2 cm. Calyx diameter: About 9 mm. Sepal length: About 2.2 cm. Sepal width, at base of "free" portion: About 4 mm. Shape: Narrowly oblong. Apex: Acute. Margin: Entire. Texture and luster, upper surface: Smooth, glabrous; glossy. Texture and luster, lower surface: Smooth, glabrous; matte. Color: When opening, upper surface: Close to 146B. When opening, lower surface: Close to NN137C. Fully opened, upper surface: Close to 146B. Fully opened, lower surface: Close to between 139A and 147A.

*Peduncles*.—Length: About 4 mm. Diameter: About 1 mm. Strength: Moderately strong. Aspect: About 15° from the stem axis, Texture and luster: Smooth, glabrous; moderately glossy. Color: Close to 137C.

*Reproductive organs*.—Stamens: Quantity: About ten stamens per flower. Filament length: About 2.3 cm. Filament color: Close to NN155D. Anther length: About 2 mm. Anther shape: Oblong. Anther color: Close to 186D. Pollen: Moderate. Pollen color: Close to 156D. Pistils: Quantity: About two per flower. Pistil length: About 2.4 cm. Stigma diameter: About 2 mm. Stigma shape: Pointed, spirally curved. Stigma color: Close to 70A to 70B. Style length: About 1.7 cm. Style color: Close to 70C to 70D; proximally, fading to close to NN155D. Ovary color: Close to 145A to 145B. Fruits and seeds: Fruit and seed development have not been observed on plants of the new Carnation.

Disease & pest resistance: Plants of the new Carnation have not been observed to be resistant to pathogens and pests common to Carnation plants.

Temperature tolerance: Plants of the new Carnation have been observed to tolerate high temperatures about 35° C. and to be suitable for USDA Hardiness Zones 5 to 9.

It is claimed:

1. A new and distinct Carnation plant named 'Hilesmay' as illustrated and described.

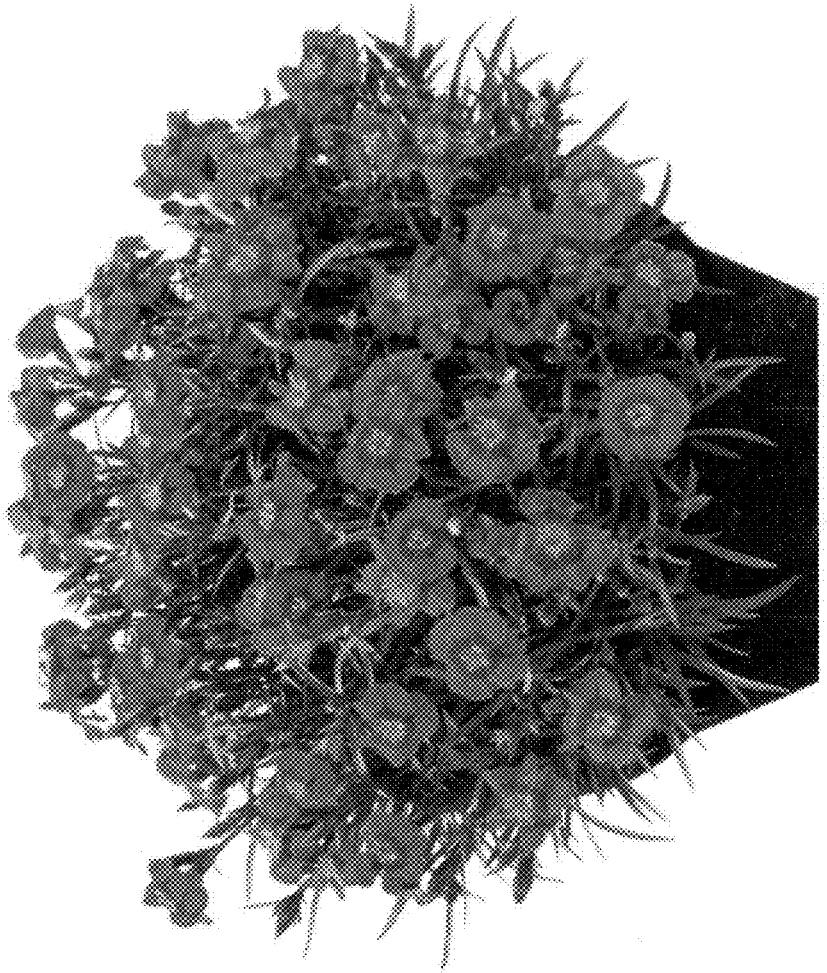

* * * * *